United States Patent [19]

Mayo et al.

[11] 4,125,115
[45] Nov. 14, 1978

[54] TOURNIQUET

[75] Inventors: John D. Mayo, Vaucluse; Laurence N. Kalnin, Bexley, both of Australia

[73] Assignee: Cecil E. Mayo Pty. Ltd., New South Wales, Australia

[21] Appl. No.: 737,037

[22] Filed: Oct. 29, 1976

[51] Int. Cl.² .............................................. A61B 17/12
[52] U.S. Cl. ......................................... 128/327; 24/78
[58] Field of Search ..................... 24/77 R, 78, 230 A; 128/327, 134

[56] References Cited

U.S. PATENT DOCUMENTS

| | | | |
|---|---|---|---|
| 256,087 | 4/1882 | Wiesenmeyer | 24/230 A |
| 348,950 | 9/1886 | Boyer | 24/230 A |
| 2,869,200 | 1/1959 | Phillips et al. | 24/78 |
| 3,013,317 | 12/1961 | Weber | 24/78 X |
| 3,958,575 | 5/1976 | Von Soiron | 128/327 |

FOREIGN PATENT DOCUMENTS 330,439 10/1935 Italy ......................................... 128/327

*Primary Examiner*—Robert W. Michell
*Assistant Examiner*—Michael H. Thaler
*Attorney, Agent, or Firm*—Oblon, Fisher, Spivak, McClelland & Maier

[57] ABSTRACT

This invention relates to an improved tourniquet. It has a semi-elastic belt fixed at one end to a tongue. The tongue is releasably engageable in a buckle. The other end of the belt passes through belt adjusting means to form a tourniquet loop. The belt adjusting means form part of the buckle. The length of the loop is adjustable as required. Slow and quick tourniquet release means are provided at the belt adjustment means and tongue engagement means, respectively.

2 Claims, 2 Drawing Figures

TOURNIQUET

BACKGROUND OF THE INVENTION

1. Field of the Invention

This invention relates to an improved tourniquet for use in restricting the circulation of blood in arteries and veins of limbs.

2. Brief Description of the Prior Art

In the prior art various types of tourniquets have been proposed and used, the simplest being a length of cord or material which is pulled tight and tied in a knot. More sophisticated tourniquets have been developed, one of which comprises a strip of material having "VELCRO" patches attached to the relevant portions so that, when the tourniquet has been pulled tight, the VELCRO patches are brought together and hold it in place.

The problem with the VELCRO type tourniquet is that it does not allow the tourniquet to be easily applied by the patient, as it takes two hands to apply the tourniquet at the required tension.

Another type of tourniquet comprises a strip of material which passes through guides and has a wedge member releasably engaging the two pieces of material to prevent them from slipping once the tourniquet has been applied. This type of tourniquet is applied by either slipping it along the arm or leg to the desired point and tightening, which is an awkward maneuver, or threading the material through the guides, which is even more awkward. A good deal of dexterity is then necessary to lock the wedge into position without it slipping and thus losing some of the tension on the tourniquet.

SUMMARY OF THE INVENTION

It is the object of this invention to provide a tourniquet that may be readily applied with the use of only one hand, which is fully adjustable throughout its useable length and can be easily released.

In its broadest form the invention comprises a tourniquet having a buckle, belt and a tongue. The buckle or tongue has means for adjusting the length of the belt and means for releasably engaging the tongue. The end of the belt remote from the adjusting means is fixed to the other member.

BRIEF DESCRIPTION OF THE DRAWINGS

The invention will now be described by way of example only with reference to the accompanying drawings wherein.

DETAILED DESCRIPTION OF THE PREFERRED EMBODIMENT

Figure 2:
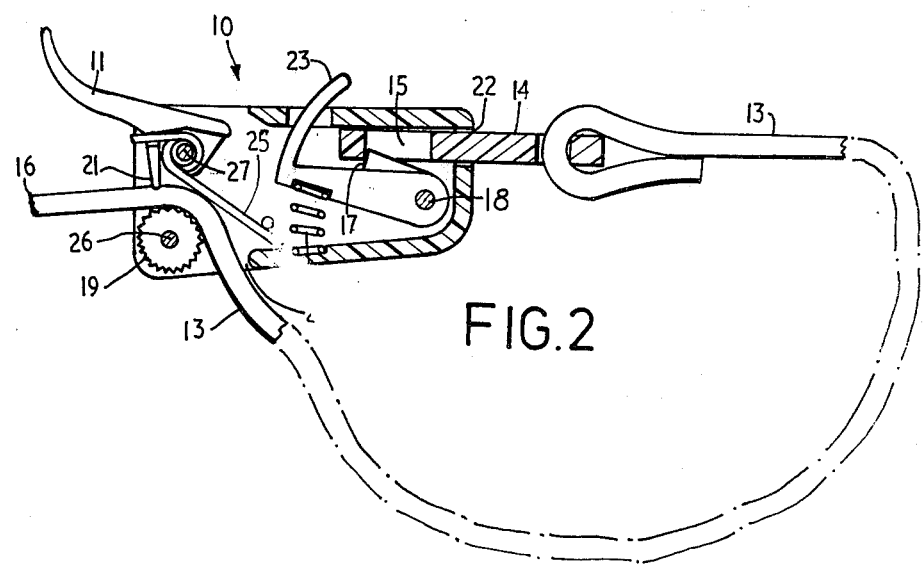
FIG. 2 is a cross sectional view of the assembled preferred form of the invention.

In accordance with the preferred form of the invention, the tourniquet has a buckle 10, a belt 13 and a tongue 14. The belt 13 has one end permanently attached to the tongue 14 while the other, or free, end 16 of the belt 13 is passed through a gap 20 in the base of the buckle 10 and around grooved roller 19 mounted in the buckle 10. The free end 16 then passes between the roller 19 and the jamming edge 21 of the belt adjustment lever 11 so that it is exposed as shown in FIG. 2.

To apply the tourniquet to a limb such as an arm or leg, the tongue 14 end of the belt 13 is passed around the limb and the tongue 14 is inserted into the tongue receiving gap 22 of the buckle 10. When that tongue is fully inserted, an opening 15 in the tongue 14 becomes engaged with the catch 17 of a tongue engagement lever 23, which prevents the tongue 14 from becoming disengaged from the buckle 10. The tongue engagement lever 23 is hingeably mounted by pin 18 near the base of buckle 10. A spring 24 urges the lever 23 towards the tongue receiving gap 22 about its hinge mounting pin 18 to maintain the catch 17 in the engaged position.

To achieve the desired tension on the tourniquet, the free end 16 of the belt 13 is then simply pulled, thus drawing the tourniquet firmly around the limb.

Once the desired tension has been achieved, the lever 11, which is biased by means of spring 25, urges the jamming edge 21 towards the roller 19 to prevent the belt 13 slipping from its tensioned position.

The gap between the jamming edge 21 and the outer surface of the roller 19 is less than the thickness of the belt 13. Alternatively, the distance between the jamming edge and its pivot point may be greater than the distance between the outer surface of the roller 19 and the pivot point of the jamming edge 21.

Other types of adjustment means, such as alligator teeth jaws, may be used in place of the roller and/or jamming edge, if very high loads are to be applied. The belt 13 is preferably made of an elastic or semi-elastic material, instead of a non extensible material, so that it can be stretched to maintain the tension even if the limb expands or contracts slightly. To release the tourniquet without a violent contraction of the elastic, the lever 11 is lifted to disengage the jamming edge 21 from the belt 13. Thus, the elastic will gradually contract due to the friction of the belt passing around the roller 19. If, however, a quick release is necessary, the tongue engagement lever 23 is simply depressed so that it rotates about its pivot mounting 18. The catch 17 disengages the opening 15 in the tongue 14, the elastic contracts quickly and extracts the tongue 14 from the buckle 10.

Figure 1:
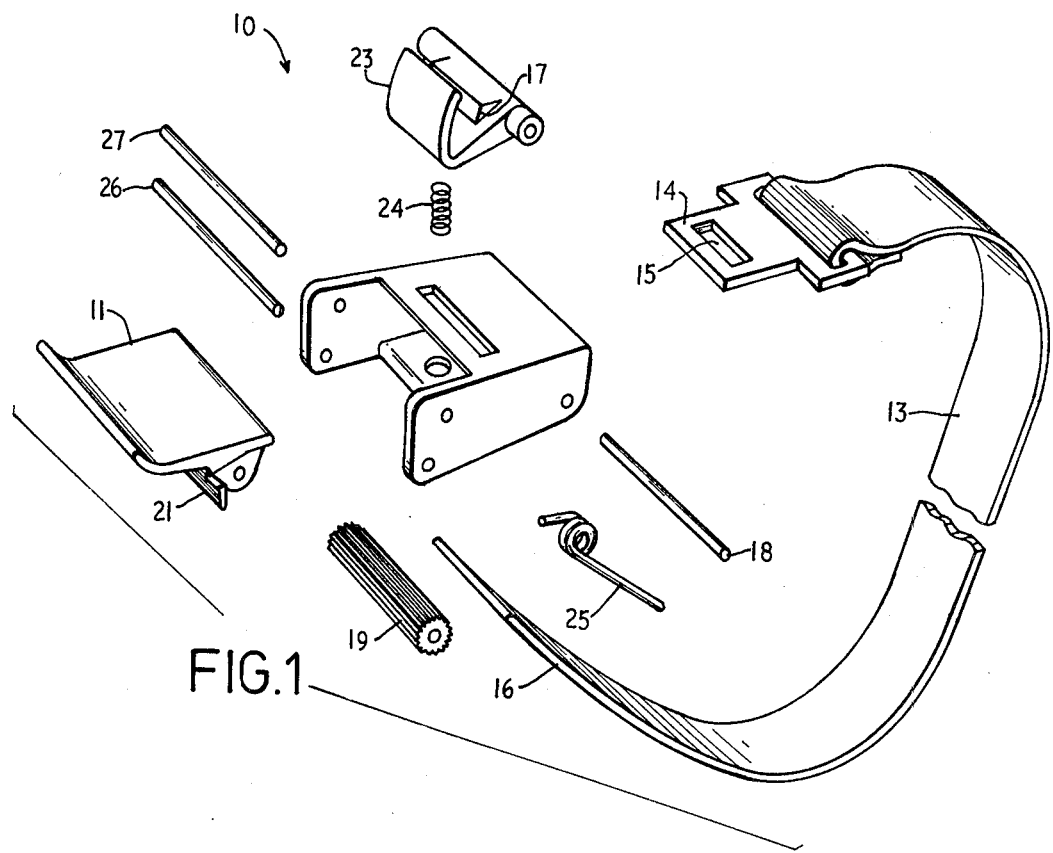
FIG. 1 is an exploded view of the preferred form of the invention.

It will be noted that in the preferred embodiment, as shown in FIGS. 1 and 2, the lever 23 is curved. This allows for simple release by one finger of the user without any awkward manipulation by the hand.

It will also be obvious that the belt adjustment means defined by the lever 11, roller 19 and jamming edge 21 may be mounted on the tongue 14, in which case the belt would be fixed to the buckle 10 and adjustable at the tongue 14.

What we claim is:

1. A tourniquet comprising:
   a buckle comprising a hollow housing having a plurality of openings therein;
   a tongue adapted to be receivably engaged within one of said openings in said buckle; and
   a belt fixedly attached at one end of said tongue, with the other end of said belt being adapted to be inserted through another of said openings in said buckle;
   said buckle having resiliently biased means therewithin for releasably engaging the portion of said belt passing therethrough, said belt engaging means within said buckle comprising a roller and an opposing spring biased releasable jamming edge, said other end of said belt is adapted to pass around a portion of the circumference of said roller to be pinched between said roller and said jamming edge such that said belt may be passed freely around said roller in one direction so as to reduce the length of the tourniquet portion of said belt and is prevented from movement in the reverse direction without release of the jamming edge, which is attached to a pivotally mounted lever which is urged by resilient biasing means to engage said jamming edge with said belt, said lever projecting outwardly of said housing;

whereby the effective length of the tourniquet formed by said belt is readily adjusted;

said tongue having an opening in the part thereof receivable in said buckle;

said buckle also having means therewithin for releasably engaging said tongue, including a lever, a catch on said lever for engaging said opening in said tongue, means for resiliently biasing said lever to move in a given direction for urging said catch to engage said opening of said tongue when said tongue is inserted therein, and a portion of said lever being exposed to the outside of said buckle for enabling manual movement thereof against said biasing means for releasing the engagement of said catch with said tongue.

2. The tourniquet of claim 1 wherein the belt is made of a semi-elastic material.

* * * * *